United States Patent [19]

Brooks et al.

[11] Patent Number: 4,668,668

[45] Date of Patent: May 26, 1987

[54] COMPOSITIONS INHIBITING MURINE MXT DUCTAL CARCINOMA

[75] Inventors: Samuel C. Brooks, Orchard Lake; Jerome P. Horwitz, Oak Park, both of Mich.

[73] Assignee: Wayne State University, Detroit, Mich.

[21] Appl. No.: 825,760

[22] Filed: Feb. 3, 1986

Related U.S. Application Data

[63] Continuation-in-part of Ser. No. 741,125, Jun. 4, 1985, which is a continuation of Ser. No. 591,500, Mar. 20, 1984, Pat. No. 4,568,673.

[51] Int. Cl.$^4$ .............................................. A61K 31/56
[52] U.S. Cl. .................................................... 514/178
[58] Field of Search ................................. 514/178, 177

[56] References Cited

U.S. PATENT DOCUMENTS

| | | | |
|---|---|---|---|
| 3,377,362 | 4/1968 | Cantrall et al. | 260/397.4 |
| 3,526,648 | 9/1970 | Bertin et al. | 260/397.45 |
| 4,340,602 | 7/1982 | Brooks | 424/238 |
| 4,496,555 | 1/1985 | Brooks et al. | 260/397.5 |
| 4,522,758 | 6/1985 | Ward et al. | 260/397.5 |

OTHER PUBLICATIONS

Rozhin et al, "Proc. Am. Assoc. Cancer Research", No. 21 (1980), p. 260.
Rozhin et al, Cancer Res., 43:2611–2617 (Jun., 1983).
Neeman et al, J. Med. Chem., 1983:465–469 (1983).
Utne et al, J. Org. Chem., 33:2469–2473 (1968).
Iyer et al, J. Org. Chem., 47:644 (1982).
Iyer et al, J. Med. Chem., 28:162 (1983).
Brooks et al, J. Toxic. and Environ. Health, 4:283–300 (1978).
Rozhin et al, J. Biol. Chem., 252:7214–7220 (1977).
Pack et al, Endocrinology, 95:1680–1690 (1974).

Primary Examiner—Leonard Schenkman
Assistant Examiner—Joseph A. Lipovsky
Attorney, Agent, or Firm—John S. Roberts, Jr.

[57] ABSTRACT

A compound of the formula

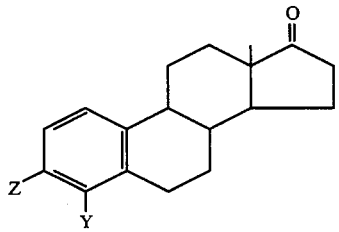

wherein Z is alkoxy of 1–4 carbon atoms and Y is amino, inhibits the growth of murine ductal carcinoma (MXT mammary tumors). A compound wherein Z is OH and Y is nitro, administered orally, inhibits the growth of MXT mammary tumors.

5 Claims, No Drawings

COMPOSITIONS INHIBITING MURINE MXT DUCTAL CARCINOMA

REFERENCE TO RELATED APPLICATIONS

This application is a continuation-in-part of Brooks et al., Ser. No. 741,125, filed June 4, 1985, which is a continuation of Brooks et al., Ser. No. 591,500, filed Mar. 20, 1984, now U.S. Pat. No. 4,568,673.

BACKGROUND OF THE INVENTION

This invention relates to the inhibition of hormone-dependent mammary tumors, such as those induced by 7,12-dimethylbenz(a)anthracene or transplantable ductal carcinoma (MXT murine type), by compounds known to be inhibitors of estrogen sulfotransferase.

Estrogen sulfotransferase inhibitors, such as 4-nitroestrone 3-methyl ether, are expected to prevent implantation of a blastocyst in the epithelial uterine lining of a pregnant female. Accordingly, these compounds may function as contragestative agents, Brooks U.S. Pat. No. 4,340,602.

A member of this group of compounds, 4-nitroestrone 3-methyl ester also has been found to inhibit the growth of hormone dependent mammary tumors, induced by 7,12-dimethylbenz(a)anthracene, Rozhin et al., *Proc. Am. Assoc. Cancer Res.*, 21:260 (1980). It has been found that the utility of 4-nitroestrone 3-methyl ether is essentially limited to parental administration, particularly intraperitoneal or subcutaneous injection thereof.

It is an object of this invention to provide compounds which are active against hormone-dependent mammary tumors, other than those induced by 7,12-dimethylbenz-(a)anthracene, and to provide compounds which are active when administered orally.

PRIOR ART STATEMENT

Brooks, in U.S. Pat. No. 4,340,602, herein incorporated by reference, has proposed that derivatives of 2- and/or 4-bromo- or nitro-estradiol or estrone, having an etherified hydroxyl function at the 3-position are active inhibitors of estrogen sulfotransferase activity. The active compounds should act to prevent implantation of a blastocyst in the epithelial uterine lining of a female mammal.

Cantrall et al (U.S. Pat. No. 3,377,362) indicate that 1-halo-3-methoxy-estra-1,3,5(10)-triene-17-one and related compounds have estrogenic, hypocholesteremic and protein anabolic activity.

Δ1,3,5(10)-Gonatrienes having an 11 beta-alkoxy substituent, wherein the 2-substituent is H, halogen or methyl; the 3-substituent is H, alkoxy or acyloxy; the 4-substituent is H, halo or lower alkyl; and the 17-substituent is =O or

are disclosed by Bertin et al., U.S. Pat. No. 3,526,648, as having estrogenic activity.

Pertinent literature references include:

Rozhin et al., "Effects of 4-Nitroestrone 3-Methyl Ether or Dimethylbenz(a)anthracene-induced Mammary Tumors," *Cancer Res.*, 43:2611–2617 (June, 1983).

Rozhin et al., "Effect of an Inhibitor of Estrogen Sulfurylation, 4-Nitroestrone 3-Methyl Ether on Mammary Tumor Growth," *Proc. Am. Assoc. Cancer Res.*, 21:260 (1980).

Neeman et al., "Modified Steroid Hormones. 7. 4-Fluoro-17-beta-estradiol: Carbon-13 Nuclear Magnetic Resonance, Crystal and Molecular Structure, and Biological Activity," *J. Med. Chem.*, 1983:465–469 (1983).

Utne et al., "The Synthesis of 2- and 4-Fluoroestradiol," *J. Org. Chem.*, 33:2469–2473 (1968).

Iyer et al., *J. Org. Chem.*, 47:644 (1982) and *J. Med. Chem.*, 28:162 (1983).

Brooks et al., "Role of Sulfate Conjugation in Estrogen Metabolism and Activity," *J. Toxic. and Environ. Health*, 4:283–300 (1978).

Rozhin et al., "Studies on Bovine Adrenal Estrogen Sulfotransferase: II. Inhibition and Possible Involvement of Adenine-estrogen Stacking," *J. Biol. Chem.*, 252:7214–7220 (1977).

Pack et al., "Cyclic Activity of Estrogen Sulfotransferase in the Gilt Uterus," *Endocrinology*, 95:1680–1690 (1974).

SUMMARY OF THE INVENTION

This invention relates to a composition which inhibits the growth of hormone dependent MXT mammary tumors, comprising a compound of the formula

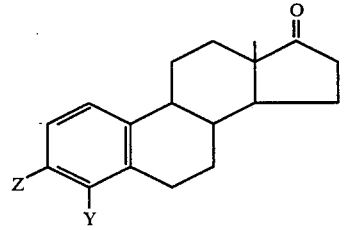

wherein Z is alkoxy of 1–4 carbon atoms and Y is amino, in admixture with a pharmaceutically acceptable carrier. This invention further relates to a composition for oral administration to mice to inhibit the growth of murine MXT ductal carcinoma, comprising a compound of the foregoing formula, wherein Z is hydroxy and Y is nitro, in admixture with a pharmaceutically acceptable carrier.

This invention further relates to a method of inhibiting the growth of MXT murine ductal carcinoma by administering to mice being treated an amount of one of the foregoing compounds, effective to inhibit growth of MXT ductal carcinoma.

DETAILED DESCRIPTION OF THE INVENTION

One group of compounds of this invention are ethers of the 3-hydroxy function of 4-aminoestrone. Therefore, in the formulas of this disclosure, Z is alkoxy of 1–4 carbon atoms. This group of ethers includes methoxy, ethoxy, propoxy and butoxy compounds, including the various possible isomers.

When the compounds disclosed are administered subcutaneously, a preferred compound is 3-methoxy-4-amino estrone. For oral administration, 4-nitroestrone is preferred.

SYNTHESIS AND EVALUATION SECTION

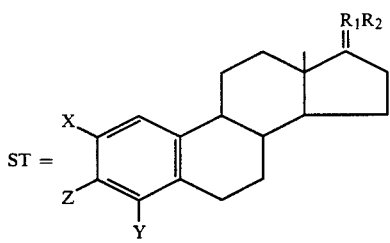

In the specification, ST represents an estra-1,3,5(10)-triene residue and substituents X, Y, Z, R, and $R_2$ are as indicated in each case.

A readily separable mixture of 2- and 4-nitroestrone is obtained by nitration of estrone (ST; Z=OH, $R_1+R_2=O$) with a stoichiometric amount of nitric acid in glacial acetic acid. See, generally, Werbin et al., *J. Biol. Chem.*, 223:651 (1965); Kraychy, et al., *J. Am. Chem. Soc.*, 79:754 (1957); Pickering, et al., *Ibid*, 80:680 (1958); and Tomson, et al., *J. Org. Chem.*, 24:2056 (1959).

2-Amino- and 4-aminoestrone are obtained by reduction of the corresponding nitroestrone with sodium hydrosulfite ($Na_2S_2O_4$) in actone-aqueous alkali solution by the technique of Kratchy et al., supra.

Aminoestrone 3-O-methyl esters are prepared, starting from 2-nitro or 4-nitroestrone, by treatment with methyl iodide/potassium carbonate to give a corresponding 3-O-methyl ether, which is reduced catalytically using W-2 Raney nickel or chemically using sodium hydrosulfite to a corresponding amino compound.

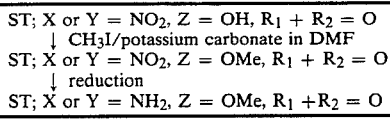

ST; X or Y = $NO_2$, Z = OH, $R_1 + R_2 = O$
↓ $CH_3I$/potassium carbonate in DMF
ST; X or Y = $NO_2$, Z = OMe, $R_1 + R_2 = O$
↓ reduction
ST; X or Y = $NH_2$, Z = OMe, $R_1 + R_2 = O$ Methylation of the 3-hydroxyl function can be done by the method of Tomson et al., supra. Higher O-alkyl ethers can be prepared in a similar way, using the selected alkyl iodide.

Catalytic reduction can be done by the method of Tomson et al., supra, or that of Utne et al., supra. Chemical reduction can be done according to Kraychy et al., supra.

The compounds of this invention were evaluated for inhibitory activity against murine hormone-dependent mammary tumors of the MXT type or of the type induced by 7,12-dimethylbenz(a)anthracene by methods cited above.

Due to their tumor inhibiting activity, the compounds of this invention are useful for treating hormone-dependent mammary tumors in human and veterinary medicine.

The compounds of this invention can be employed in admixture with conventional excipients, i.e., pharmaceutically acceptable organic or inorganic carrier substances suitable for parenteral, enteral or topical application, which do not deleteriously react with the active compounds.

Suitable pharmaceutically acceptable carriers include but are not limited to water, salt solutions, alcohols, vegetable oils, polyethylene glycols, gelatine, lactose, amylose, magnesium stearate, talc, silicic acid, viscous parafin, perfume oil, fatty acid monoglycerides and diglycerides, pentaerythritol fatty acid esters, hydroxymethyl cellulose, polyvinyl pyrrolidone, etc.

The pharmaceutical preparations can be sterilized and, if desired, mixed with auxiliary agents, e.g., lubricants, preservatives, stabilizers, wetting agents, emulsifiers, salts for incluencing osmotic pressure, buffers, coloring, flavoring and/or aromatic substance, which do not deleteriously interact with the active compounds.

For parenteral application, solutions are particularly suitable, including oily or aqueous solutions, suspensions, emulsions, implants or suppositories. Ampoules are convenient unit dosages.

It will be understood that preferred dosages of the active compounds used will vary according to the specific compound being used, the particular compositions formulated, the mode of application, and the particular organism being treated. Optimal application rates for a given set of conditions can be ascertained by those skilled in the art using conventional dosage determination tests in view of the above guidelines.

DESCRIPTION OF MOST PREFERRED EMBODIMENT

In most preferred embodiments, 4-nitroestrone will be administered orally and 4-aminoestrone 3-O-methyl ether will be administered subcutaneously.

Without further elaboration, it is believed that one skilled in the art can, using the preceding description, utilize the present invention to its fullest extent. The following preferred specific embodiments are therefore to be construed as merely illustrative and not limitative of the remainder of the specification and claims in any way whatsoever.

EXAMPLE 1

4-Aminoestrone 3-O-Methyl Ether (ST; Y=$NH_2$, Z=OMe, X=H, $R_1+R_2=O$)

4-Nitroestrone 3-O-methyl ether was prepared according to Tomson and Horwitz, *Journal of Organic Chemistry*, 24:2056 (1959).

EXAMPLE 2

Effects of 4-Nitroestrone 3-Methyl Ether (St; Y—$NO_2$, Z=OMe, $R_1+R_2=O$) on Mammary Tumors Induced by Dimethylbenz(a)anthracene Chemicals and Reagents. Estrone, 17-betaestradiol 3-benzoate, estrone sulfate, aryl sulfatase (EC 3.1.6.1), beta-glucuronidase (EC3.2.1.31), 7,12-dimethylbenz-(a)anthracene (DMBA), and 5-fluorouracil were obtained from Sigma Chemical Co. (St. Louis, MO). 4-Nitroestrone 3-methyl ether, 4-nitroestrone, and 2,4-dinitroestrone were synthesized by the procedures of Tomson et al., supra.

Animals. Virgin female Sprague-Dawley rats (The Charles River Co., Wilmington, MA) were housed 4 to 6/cage in a light (12 hr/day—and temperature (24°)—controlled room and given a diet of Wayne Lab-Blox laboratory chow (Allied Mills, Inc., Chicago, IL) and tap water ad libitum. At 50 days of age, rats were intubated with DMBA (10 mg/100 g body weight) dissolved in sesame oil (20 mg/ml). Beginning at Day 45 after intubation, all animals were weighed and palpated once per week. Tumor volumes were calculated by measuring 2 diameters with a caliper and the third dimension with a ruler, then by substituting values:

Volume (cu cm) = 1/6 abc where a, b, and c are the 3 different diameters of the tumor. The agreement of the in vivo tumor volume and measurements of excised tumors identified at necropsy was 95 to 99%. When about 75% of rats had palpable tumors (81 to 92 days after intubation), the animals were randomized, excluding rats with tumors larger than 2.00 ml and rats with more than 5 tumors/animal. The mean initial tumor volumes in control and treated groups ranged between 0.4 and 0.9 cu cm over the various experiments. When necessary, ovariectomy (ether anesthesia) was performed on the first or second day after the initiation of the study. The significance of difference between treatment groups was examined by Student's t test.

Estrogen derivatives (>99% pure by thin-layer chromatography) were injected s.c. daily (Monday to Friday). After distribution in SSV (steroid-suspending vehicles, 0.9% NaCl solution with 0.5% sodium carboxymethyl-cellulose-7, 0.4% polysorbate; and 0.9% benzylalcohol, obtained from the National Cancer Institute), the steroids (20 mg/ml) were administered at 0.12 to 54 mg/kg body weight. The suspension was sonicated before use to achieve uniform distribution. 17-Beta-estradiol 3-benzoate was dissolved directly in sesame oil to a concentration of 2.5 mg/ml. The control group was given injections of SSV or sesame oil alone.

The toxicity of all antitumor agents was determined by comparing body weights of treated and control animals.

Postmortem Examination and Histopathology of Tumors. Rats were selected for colchicine injections (2 mg/kg body weight) 2 hr prior to necropsy to obtain an accurate measurement of mitotic indices of tumors. Animals were sacrificed with $CO_2$ gas or bled to death via the abdominal aorta. Tumors and tissues were removed and preserved in 10% neutral buffered formalin for histopathological examination. Gross anomalies of abdominal, thoracic, and cranial cavities were recorded. Uteri were removed, trimmed, and weighed fresh. Ovaries, adrenals, and pituitaries were trimmed and weighed after fixation.

Histopathological observations on hematoxylin- and iosin-stained tumor and organ sections were performed, and comparisons between the control and heated groups were carried out using computer analysis. The microscopic parameters used to judge the degree of anaplasia in DMBA-induced mammary neoplasms, when treated animals were compared to controls, were: (a) the type of epithelium or mammary tissue involved; (b) the degree of encapsulation of the neoplasm; (c) the number of mitotic figures observed; (d) the extent of stroma invasions of the neoplastic epithelium; (e) the severity of lymphocytic infiltration of the neoplasms; and (f) the regressive, degenerative, or vacuolative changes in the neoplastic epithelium. These criteria are suggested by Boylan et al., "Morphology, growth characteristics and estrogen binding capacity of DMBA-induced mammary tumors from ovariectomized rats," Br. J. Cancer, 35:602–609 (1977); Gullino et al., "Physiopathological characteristics of hormone dependent tissue," J. Natl. Cancer Inst., 49:1333–1348 (1972); Haslam et al., "Histopathogenesis of 7,12-dimethylbenz(a)anthracene induced rat mammary tumors," Proc. Natl. Acad. Sci. U.S.A., 74:4020–4024 (1977); Russo, "Pathogenesis of mammary carcinomas induced in rats by 7,12-dimethylbenz(a)anthracene," J. Natl. Cancer Inst., 49:435–445 (1977) and Strettony et al., "Spontaneous regression of induced mammary tumors in rats," Br. J. Cancer, 17:85–89 (1973). Histological examination was performed on all mammary tumors.

Results. In a series of tests using 7–10 Sprague-Dawley rats/group, subcutaneous injections of 24 mg/kg of body weight of an estrogen analog being evaluated were given for 35 days. The estrogen analogs selected were known to be superior estrogen sulfotransferase inhibitors, Rozhin et al., J. Biol. Chem., 252:7214–7220 (1977).

In Table I below, the mean values are the mean ±S.D. The following rsults were obtained:

TABLE I

| Estrogen analog injected | Mean tumor volume (cu cm) | Mean tumor no. (no. tumors/rat) |
|---|---|---|
| None | 1.48 ± 2.09 | 3.30 ± 2.60 |
| 2,4-Dibromoestrone 3-methyl ether | 1.24 ± 1.07 | 4.26 ± 2.51 |
| 2,4-Dinitroestrone | 1.14 ± 1.37 | 2.90 ± 1.67 |
| 4-Nitroestrone | 0.75 ± 0.10 | 1.95 ± 2.60 |
| 4-Nitroestrone 3-methyl ether | 0.05 ± 0.05 | 1.35 ± 0.40 |

In the table p values, when compared to those of the control tumors, were <0.05. The results for the 2,4-dibromoestrone 3-methyl ether 2,4-dinitroestrone, and 4-nitroestrone treatments were therefore insignificant.

EXAMPLE 3

Effect of Orally-Administered 4-Nitroesrone (ST; X=$NO_2$, X=H, Z=OH, $R_1+R_2$=O) on Mammary Tumors Induced by Dimethylbenz(a)anthracene The test compound was suspended in a mixture of 3% by weight of polyethoxylated castor oil, 3% by weight of ethanol and 94% by weight of water. The test compound was administered orally at a daily dosage of 130 mg/kg of body weight to mice in which murine MXT mammary ductal carcinoma had been induced as in Example 2. The controls received the suspending medium alone. Tumor size was evaluated as in Example 2.

As shown in Table II, the mice treated with 4-nitroestrone had tumors with significantly smaller median size at day 33 than the controls.

These results are unexpected in view of the results of subcutaneous administraton of 4-nitroestrone to rats, reported in Example 2.

TABLE II

Oral Treatment of Early Stage, Hormone-Dependent MXT Mouse Mammary Ductal Carcinoma

| | Control | 4-Nitroestrone |
|---|---|---|
| (p.o.) Dosage (mg/kg) | — | 130 |
| Schedule | — | QD 1-20 |
| Median Tumor Size on Day 33 | 1099 | 149 |
| T/C Value Day 33 (%) | — | 13.5 |

EXAMPLE 4

Effect of Subcutaneously Administered 4-Aminoestrone 3-O-Methyl Ether (ST; Y-NH$_2$, X=H, Y=OMe, R$_1$+R$_2$=O) on MXT Mouse Mammary Ductal Tumors Induced by Dimethylbenz(a)anthracene (a) The test compounds were suspended in a mixture of 3% by weight of polyethoxylted castor oil, 3% by weight of ethanol and 94% by weight of water and administered subcutaneously to mice in which MXT mammary tumors had been induced by dimethylbenz-(a)anthracene as in Example 2.

As shown in Table III, treating mice with 4-aminoestrone 3-O-methyl ether was more effective than no dosage (control) or than 4-nitroestrone in reducing tumor growth.

(b) Lower dosages of 4-aminoestrone 3-O-methyl ether in the same suspending agent were administered subcutaneously as above. As shown in Table IV, tumor growth in the treated mice was significantly slower than in the controls.

TABLE III

|  | Control | 4-Nitro-estrone | 4-Aminoestrone 3-O—methyl ether |
| --- | --- | --- | --- |
| (s.c.) Dosage (mg/kg) | — | 200 | 200 |
| Schedule | — | QD 1-12 | QD 1-12 |
| Time for Median Tumor to Reach 800 mg (dmp) | 25 | 76 | 82 |
| T/C Value Day 33 (%) | — | 5.5 | 3.8 |

TABLE IV

|  | Control | 4-Amino-estrone | 3-O—Methyl ether |
| --- | --- | --- | --- |
| (s.c.) Dosage (mg/kg) | — | 100 | 33 |
| Schedule | — | QD 1-19 | QD 1-19 |
| Time for Median Tumor to Reach 500 mg | 18 | 40 | 39 |
| T/C Value Day 39 (%) | — | 4.1 | 2.6 |

EXAMPLE 5

Preparation of a Longlasting Troche

Troches (1500), each weighing 750 mg, were formulated as follows:

|  | Ingredient | Grams |
| --- | --- | --- |
| (a) | 3-Methoxy-4-aminoestrone | 15.0 |
| (b) | Pectin | 370.0 |
| (c) | Gelatin | 370.0 |
| (d) | Sodium carboxymethylcellulose | 370.0 |

The ether was mixed with approximately 10 gm. of pectin. The remainder of the pectin and other ingredients were added and mixed thoroughly. The resulting mixture was compressed into capsule-shaped troches, each of which contained 10 mg of 3-methoxy-4-aminoestrone.

EXAMPLE 6

Preparation of a Hard Candy Lozenge

The following formulation can be used to prepare approximately 9,000 lozenges weighing 5.0 grams each.

|  | Ingredient | Weight |
| --- | --- | --- |
| (a) | 4-Nitroestrone | 90 gms. |
| (b) | Sodium cyclamate | 450 gms. |
| (c) | Saccharin sodium | 45 gms. |
| (d) | Cetyl diethyl benzyl-ammonium chloride | 27 gms. |
| (e) | Benzocaine | 45 gms. |
| (f) | Granular sugar | 28 gms. |
| (g) | Liquid glucose (43°) | 16.7 kgs. |
| (h) | Sour orange flavor q.s. Wild cherry flavor q.s. |  |

The granular sugar is placed into a pre-cook kettle with 14 liters of water. The mixture is brought to a boil and the sodium cyclamate is added and dissolved with stirring. Glucose is added and the mixture brought to a predetermined temperature of 135° C.

The composition is transferred to a continuous vacuum cooker and reduced to a proper consistency for a candy base, to which the remaining ingredients are added with stirring. The mixture is thoroughly kneaded and a continuous rope formed. Lozenges weighing about 5.0 gm. each and containing about 10.0 mg. of the 4-nitroestrone are cut from the rope, packaged and distributed in any convenient manner.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and intended to be, within the full range of equivalence of the following claims.

We claim:

1. A method for inhibiting the growth of MXT murine ductal carcinoma comprising administering to mice being treated a compound of the formula

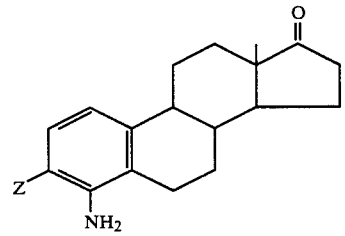

wherein Z is alkoxy of 1-4 carbon atoms, in admixture with a pharmacologically and physiologically acceptable carrier, in an amount sufficient to inhibit the growth of the ductal carcinoma.

2. The method of claim 1, wherein Z is methoxy.

3. The method of claim 1, wherein the compound is administered subcutaneously.

4. The method of claim 3, wherein Z is methoxy.

5. A method for inhibiting the growth of MXT murine ductal carcinoma comprising administering orally to mice being treated a compound of the formula

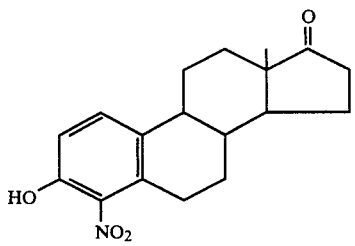
in admixture with a pharmacologically and physiologically acceptable carrier, in an amount sufficient to inhibit the growth of the ductal carcinoma.
* * * * *